(12) United States Patent
Connell et al.

(10) Patent No.: US 6,888,360 B1
(45) Date of Patent: May 3, 2005

(54) SURFACE MOUNT TECHNOLOGY EVALUATION BOARD HAVING VARIED BOARD PAD CHARACTERISTICS

(75) Inventors: David James Connell, Brantford (CA); Beverly Howard Christian, Waterloo (CA)

(73) Assignee: Research In Motion Limited, Waterloo (CA)

( * ) Notice: Subject to any disclaimer, the term of this patent is extended or adjusted under 35 U.S.C. 154(b) by 0 days.

(21) Appl. No.: 10/781,887

(22) Filed: Feb. 20, 2004

(51) Int. Cl.[7] .............................................. G01R 31/02
(52) U.S. Cl. ...................................... 324/754; 324/760
(58) Field of Search ................................ 324/754–755, 324/757–758; 174/260–261, 250; 361/684, 774, 767; 439/71, 74, 91

(56) References Cited

U.S. PATENT DOCUMENTS

| | | | |
|---|---|---|---|
| 4,467,638 A | | 8/1984 | Greenstein |
| 4,529,116 A | | 7/1985 | Gutbier |
| 5,457,880 A | | 10/1995 | McKinley et al. |
| 5,827,951 A | | 10/1998 | Yost et al. |
| 5,862,973 A | | 1/1999 | Wasserman |
| 5,926,696 A | * | 7/1999 | Baxter et al. ............... 438/118 |
| 6,013,877 A | * | 1/2000 | Degani et al. .............. 174/264 |
| 6,020,749 A | * | 2/2000 | Morris et al. ............... 324/755 |
| 6,040,530 A | * | 3/2000 | Wharton et al. ............ 324/409 |
| 6,286,208 B1 | * | 9/2001 | Shih et al. ..................... 29/879 |
| 6,300,781 B1 | * | 10/2001 | Yap et al. .................... 324/755 |
| 6,476,629 B1 | * | 11/2002 | Bjork .......................... 324/765 |
| 6,564,986 B1 | * | 5/2003 | Hsieh ......................... 324/73.1 |
| 6,600,233 B2 | * | 7/2003 | Yeoh et al. .................. 257/779 |
| 6,700,800 B2 | * | 3/2004 | Combs et al. .............. 174/260 |
| 2003/0041753 A1 | | 3/2003 | Regner et al. |
| 2003/0057264 A1 | | 3/2003 | Yoshikawa et al. |

FOREIGN PATENT DOCUMENTS

| | | |
|---|---|---|
| DE | 199 10 407 A1 | 9/2000 |
| EP | 0 779 774 A1 | 6/1997 |
| EP | 0 926 930 A2 | 6/1999 |
| JP | 03244188 | 10/1991 |
| JP | 05200991 | 8/1993 |
| JP | 10256722 | 9/1998 |
| WO | WO 98/42167 | 9/1998 |

OTHER PUBLICATIONS

Heraeus Benchmarker II Pad Geometries and Dimensions. www.bomir.com/online/indexphp?sub =249.
Lathrop, Richard R. et al., The SMT Process Benchmarking Toolkit, Heraeus.
Lathrop, Richard, "Defining Solder Paste Performace via Novel Quantitative Methods", APEX 2003.
Heraeus SMT Test Boards OSP and AU.

* cited by examiner

Primary Examiner—David Zarneke
Assistant Examiner—Jermele Hollington
(74) Attorney, Agent, or Firm—Bereskin & Parr

(57) ABSTRACT

This invention provides an evaluation board for evaluating one or more aspects of a surface mount technology system. In one aspect, the evaluation board has a substrate with at least one surface. A plurality of board pad patterns, each including a plurality of board pads, is formed on the surface. The different board pad patterns may have different shaped, sized and spaced board pads, allowing the characteristics of a surface mount technology to be tested on some or all of the board pad patterns at the same time and under uniform conditions. In another aspect, the surface may have a plurality of area-filled board pads similarly allowing a surface mount technology to be tested on the various area-filled board pads.

17 Claims, 6 Drawing Sheets

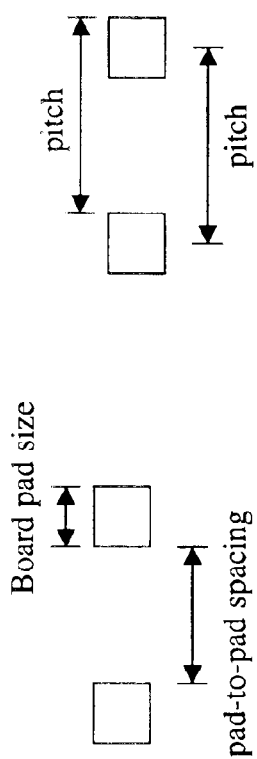
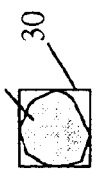
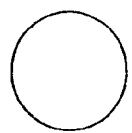

SURFACE MOUNT TECHNOLOGY EVALUATION BOARD HAVING VARIED BOARD PAD CHARACTERISTICS

FIELD OF THE INVENTION

The invention relates to an evaluation board that can be used to evaluate certain aspects of the surface mount technology process. More particularly, this invention relates to an evaluation board that can be used to evaluate solder paste, stencil and circuit board manufacturing, and the printing and reflow processes used in surface mount technology.

BACKGROUND OF THE INVENTION

Electronic devices are typically manufactured by mounting electronic components on a printed circuit board (PCB) using surface mount technology (SMT). The electronic components generally have leads, balls or conductive pads (i.e. component pads) that make electrical and mechanical contact with corresponding conductive pads (i.e. board pads) on a surface of a PCB. The process that is used for attaching the electronic components to the PCB includes the stages of solder paste deposition (i.e. printing) on the PCB through a stencil, component placement on the pasted PCB and reflow or heating the PCB. For a double-side PCB, the PCB is then turned upside down and these steps are performed again.

The PCB is manufactured by a circuit board manufacturer according to the specifications that are provided by an electronic device manufacturer. Likewise, the stencil is manufactured by a stencil manufacturer according to the specifications that are provided by the electronic device manufacturer.

Solder paste deposition involves the use of a screen printer for depositing solder paste on the board pads that are located on the surface of the PCB. In this stage, the stencil is positioned over the surface of the PCB that contains the board pads with the stencil being aligned with the PCB in a predetermined orientation. The stencil has a thickness and apertures with specific tolerances. A squeegee blade, or a Proflow™ or Rheometric™ pump, or a dispensing needle, as is commonly known to those skilled in the art, is then used to apply the solder paste to the PCB through the stencil.

Component placement includes placing electronic components, such as QFPs (quad flat package), SOPs (small outline package), chips, BGAs (Ball Grid Array), CSPs (Chip Scale Package), and the like, on the surface of the PCB such that the leads or component pads of each of the electronic components align with the corresponding board pads covered with solder paste or paste flux on the PCB surface. The reflow process consists of inserting the PCB into a reflow furnace and using a certain reflow profile for heating the PCB to cause the solder paste, and any solder that makes up part of the board pad and/or lead finish, to melt and then allowing the PCB to cool such that the solder solidifies and there is mechanical and electrical contact between component pads and the corresponding board pads. The amount of heat that is applied and the length of the heating and cooling period in the reflow profile depend on the type of solder paste that is used, the thermal mass of the product, component temperature limitations and line cycle time.

Manufacturing defects can occur during the solder paste deposition, component placement and reflow stages of the SMT process. However, typically 60 to 70% of the defects occur during the solder paste deposition stage. Accordingly, it is necessary to routinely inspect the deposited solder paste on the PCB to determine if there are any defects such as missing solder paste, improper solder paste coverage on a board pad and solder paste bridging. These defects may occur for a variety of reasons. For instance, the particular solder paste that is used may not be suitable for adhering to a board pad on the PCB given the operating conditions used in the solder paste deposition stage or the stencil may be clogged. Alternatively, there may be too much or too little solder paste that is deposited. Once again this depends on the type of solder paste used and/or the operating conditions of the solder paste deposition process. If too much solder paste is deposited, then the board pad may be in electrical contact with more than one component pad on the electronic component following the reflow process. Also, solder paste on adjacent board pads on the PCB may merge together thereby forming an electrical short circuit or bridge between the adjacent board pads. If too little solder paste is deposited, then poor mechanical and/or electrical contact between the board pad and the corresponding component pad may result. Other defects which may occur includes voids, which are bubbles that are suspended in solidified solder. A void is formed from entrapped air and/or outgasing of materials from at least one of the board pads, the component pads and solvents from the solder paste.

In addition, in surface mount technology, there is an increasing drive towards electronic components that are smaller, cheaper and provide more functionality. Accordingly, an increased number of smaller electronic components are incorporated onto one or both surfaces of a PCB. These smaller electronic components have smaller component pad sizes and smaller pad-to-pad spacing (i.e. the distance between adjacent component pads). This size reduction has stretched the capabilities of screen printing equipment and solder paste and increased the incidence of defects in the SMT manufacturing process. Accordingly, this size reduction has required changes in the various stages of the SMT process such as using a suitable solder paste and being able to deposit the solder paste on smaller board pads.

SUMMARY OF THE INVENTION

In one aspect, the present invention provides an evaluation board for evaluating one or more aspects of a surface mount technology system, the board comprising: a substrate having a surface; and a plurality of board pad patterns formed on the surface, wherein each of the board pad patterns includes a plurality of board pads.

In another aspect, the invention additionally provides an evaluation board wherein, in each of the board pad patterns, the board pads have a uniform shape, size and pad-to-pad spacing.

In another aspect, the invention provides an evaluation board wherein the size of board pads of at least some of the board pad patterns differs from the size of board pads in at least some of the other board pad patterns.

In another aspect, the invention provides an evaluation board wherein the pad-to-pad spacing of board pads of at least some of the board pad patterns differs from the pad-to-pad spacing of board pads in at least some of the other board pad patterns.

In another aspect, the invention provides an evaluation board wherein at least some of the board pad patterns are arranged in a matrix wherein the size of board pads in adjacent board pad patterns progressively changes.

In another aspect, the invention provides an evaluation board wherein at least some of the board pad patterns are arranged in a matrix wherein the pad-to-pad spacing of board pads in adjacent board pad patterns progressively changes.

In another aspect, the invention provides an evaluation board wherein at least some of the board pads patterns are arranged in a two dimensional matrix having rows and columns of board pad patterns, and wherein in each row of the matrix, a first characteristic of the board pads in the board pad pattern is varied and wherein in each column of the matrix, a second characteristic of the board pads in the board pad patterns is varied.

In another embodiment of this aspect, the invention provides an evaluation board wherein the first characteristic is selected from the group consisting of: the shape, size, and pad-to-pad spacing of the board pads; and wherein the second characteristic is chosen from the group consisting of: the shape, size, and pad-to-pad spacing of the board pads, and wherein the first and second characteristics are different.

In another aspect, the invention provides an evaluation board wherein the substrate has two surfaces and wherein each surface has a plurality of board pad patterns formed on it.

In another aspect, the invention provides an evaluation board wherein the substrate has two surfaces and wherein the first surface has a plurality of board pad patterns formed of board pads and wherein the second surface has a plurality of board pads.

In a second aspect, the present invention provides an evaluation board for evaluating one or more aspects of a surface mount technology system, the board comprising: a) a substrate having a surface; and, b) a plurality of board pad patterns formed on the surface, wherein each of the board pad patterns includes one of: an area-filled board pad or a plurality of board pads.

In another aspect, the present invention provides an evaluation board in which each of the board pad patterns includes an area-filled board pad and the size of the area-filled board pad of at least some of the board pad patterns differs from the size of board pads in at least some of the other board pad patterns.

In another aspect, the present invention provides an evaluation board, wherein each of the board pad patterns includes an area-filled board pad and the pad-to-pad of successive area-filled board pads differs from the pad-to-pad spacing of area-filled board pads in at least some of the other board pad patterns.

In another aspect, the present invention provides an evaluation board, wherein at least some of the board pad patterns are arranged in a matrix wherein the size of area-filled board pads in adjacent board pad patterns progressively changes.

In another aspect, the present invention provides an evaluation board, wherein at least some of the board pad patterns are arranged in a matrix wherein the pad-to-pad spacing of area-filled board pads in adjacent board pad patterns progressively changes.

BRIEF DESCRIPTION OF THE DRAWINGS

For a better understanding of the present invention and to show more clearly how it may be carried into effect, reference will now be made, by way of example only, to the accompanying drawings which show an exemplary embodiment of the present invention and in which:

FIG. 3 is a graphical illustration of terminology used to describe board pads on the evaluation board of the present invention;

FIGS. 4a–4e are a series of diagrams showing several cases of solder paste deposition on a board pad;

FIGS. 5a–5g are a series of diagrams showing several different embodiments for the board pads on the evaluation board.

DETAILED DESCRIPTION OF THE INVENTION

Figure 1:
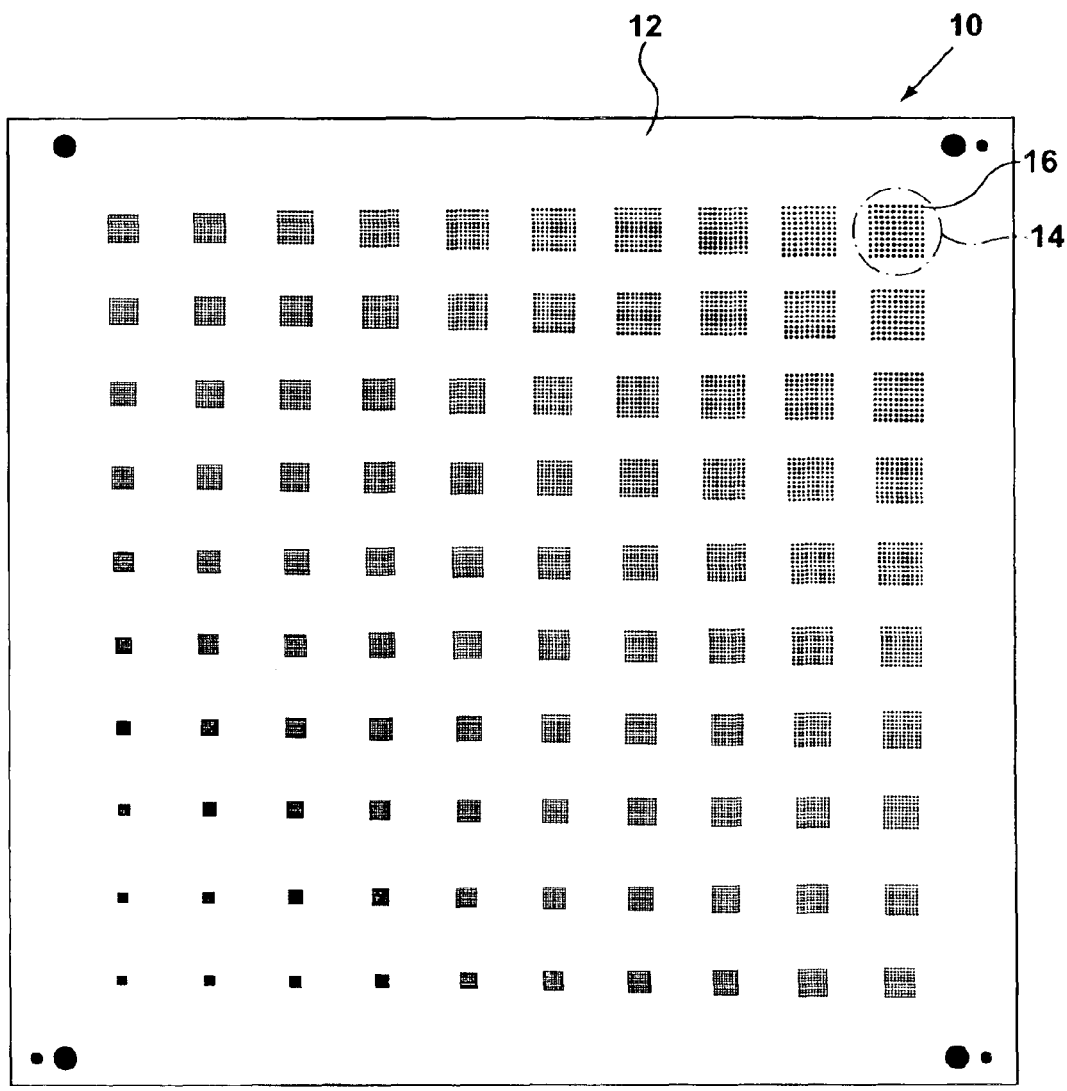
FIG. 1 is a top view of a surface of an evaluation board in accordance with the present invention.

Referring first to FIG. 1, shown therein is a top view of an evaluation board 10 for surface mount technology in accordance with the present invention. Evaluation board 10 provides a substrate for a surface 12. On surface 12, there are a plurality of board pad patterns 14. Each board pad pattern 14 comprises a plurality of board pads 16 (only one board pattern and only one board pad is labeled for simplicity). Each board pad 16 is a conductive metallic material such as copper or gold which is provided on the surface 12 of the evaluation board 10 using circuit board manufacturing techniques that are well known to those skilled in the art. Each board pad 16 may have a rectangular, paralleliped, square, circular or other shape as illustrated in FIGS. 5a–5g. Alternatively, some of the board pads 16 on the evaluation board 10 may have a rectangular shape while others may have a square, paralleliped or circular shape. The shape can be chosen to correspond with the shape of the component pads (i.e. circular-shaped pads are suitable for BGAs and CSPs).

There are a number of board pads 16 in each board pad pattern 14 to facilitate the generation of test statistics. In the exemplary evaluation board 10, there are 100 board pads 16 in a given board pad pattern 14. However, the same number of board pads 16 does not have to be used in each board pad pattern 14 on the evaluation board 10.

The evaluation board 10 is designed such that the size of the board pads 16 in the board pad patterns 14 (i.e. hereafter referred to as the board pad size) and the pad-to-pad spacing of the board pads 16 in the board pad patterns 14 are varied over the surface of the evaluation board 10. FIG. 3 provides an illustrative explanation of board pad size and pad-to-pad spacing. In the particular exemplary embodiment of the evaluation board 10 shown in FIG. 1, referenced such that board pad pattern 16 is at the upper right-hand corner, a matrix of board pad patterns 14 is provided in which, for a given row, the board pad size in a given board pad pattern is constant and the pad-to-pad spacing used in successive board pad patterns 14 is reduced in size while moving from right to left. For a given column of the matrix, the board pad size for successive board pad patterns 14 is reduced while moving from top to bottom and the pad-to-pad spacing used in each board pad pattern 14 remains constant. Accordingly, it should be understood that when moving along a straight horizontal line (i.e. row) from the bottom left of FIG. 1, that the pad-to-pad spacing is increased by 0.05 mm (in this example) along successive boards patterns while the pad size stays constant. It should also be understood that when moving along a straight vertical line (i.e. column) from the bottom of FIG. 1, that the pad size is increased by 0.05 mm (in this example) along successive board patterns while the pad-to-pad spacing stays constant. It should also be understood that if pitch is a factor that is to be looked at, in the matrix of FIG. 1, diagonal lines can be drawn along pads that have the same pitch with differing pad sizes.

The variation in board pad size and pad-to-pad spacing allows for testing the SMT process for producing electronic devices of various sizes. For instance, the board pad size and pad-to-pad spacing may be varied from a size that is larger than those that are currently used in electronic device manufacturing, to sizes that are currently used in electronic device manufacturing, to smaller sizes that will be used for future electronic device manufacturing. This allows the evaluation board 10 to be used for future generations of surface mount technology. An exemplary range of values for board pad size and pad-to-pad spacing that can be used with the evaluation board 10 is approximately 0.5 mm to 50 µm. This range includes the industry standard that is currently used which is a board pad size of 0.25 mm and a pad-to-pad spacing of 0.3 mm for the current CSP and mini BGA package types. By incorporating very small board pad sizes and pad-to-pad spacing, the evaluation board 10 also can be used to test various stages of the SMT process for failure such as the solder paste that is used, and the ability of the circuit board manufacturers and stencil manufacturers to respectively provide circuit boards and stencils to accommodate such small board pad sizes and pad-to-pad spacings. This allows for the determination of which solder paste, stencil and or circuit board designs and manufacturers are suitable for current or future electronic products.

Figure 2:
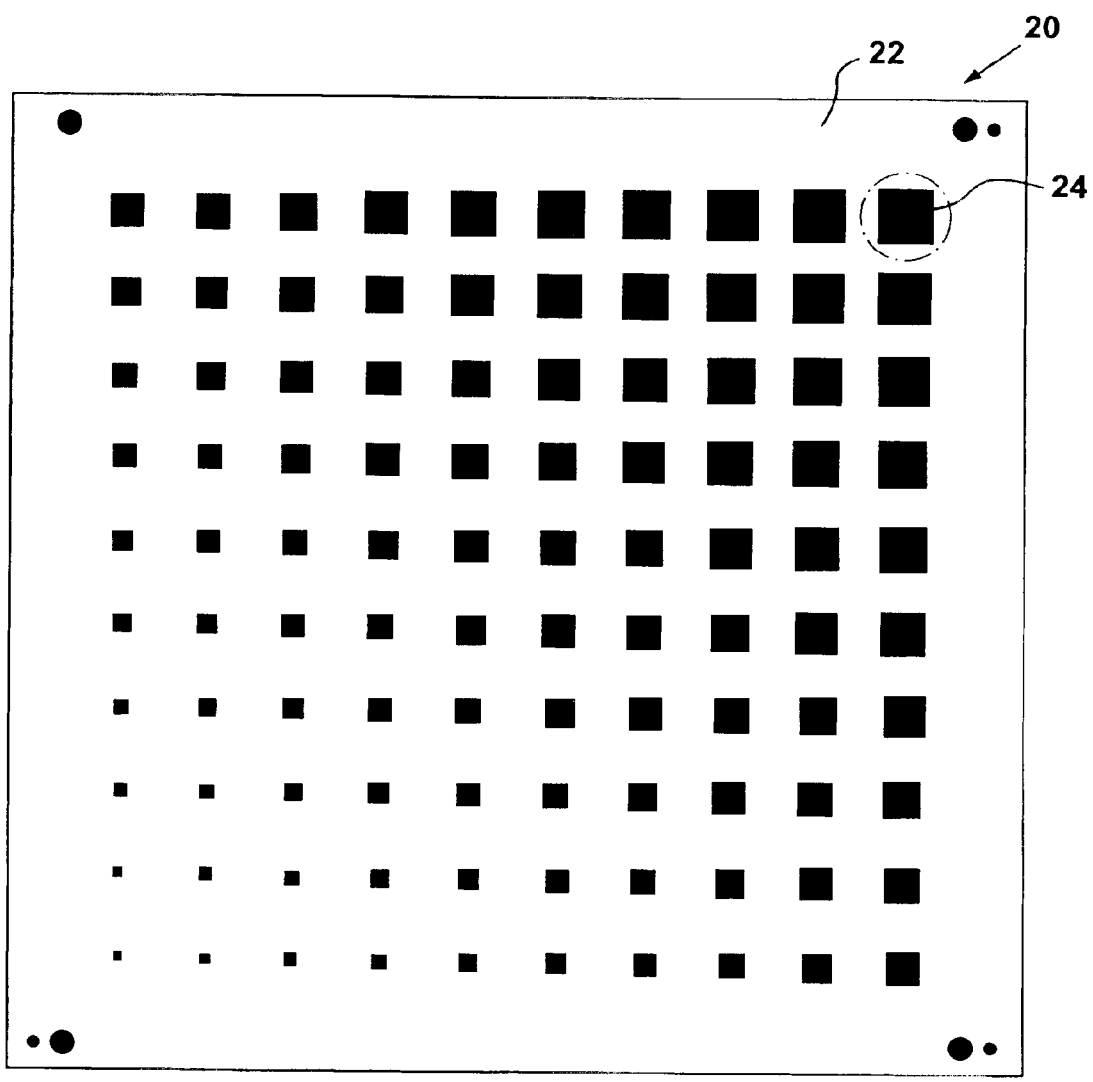
FIG. 2 is a top view of a surface of an alternative embodiment of an evaluation board in accordance with the present invention.

Referring now to FIG. 2, shown therein is an alternate embodiment of an evaluation board 20 in accordance with the present invention. On a surface 22 of the evaluation board 20, there are a plurality board pad patterns that have been filled in. The board pad patterns are referred to as area-filled pads 24, one of which is labeled for simplicity. Each area-filled pad 24 is a conductive metallic material such as copper or gold and may have a rectangular, parallelpiped, square, circular or other shape (see FIGS. 5a–5g). Alternatively, some of the area-filled pads 24 on the evaluation board 20 may have a rectangular shape while others may have a square, parallelpiped or circular shape.

In the particular exemplary embodiment of the evaluation board 20 shown in FIG. 2, a matrix of area-filled pads is provided in which, for a given row, the size of the area-filled pad is reduced while moving from right to left whereas for a given column of the matrix, the size of the area-filled pad is reduced while moving from top to bottom. The size of the area-filled pads 24 may correspond to the sizes of the board pad patterns 14 of evaluation board 10. In addition, in the example of FIG. 2, the pad-to-pad spacing of the area-filled pads is reduced along both the row and columns of the matrix. However, this need not be the case, and the same pad-to-pad spacing can be used along a given direction (i.e. row or column) of the matrix.

Figure 6A:
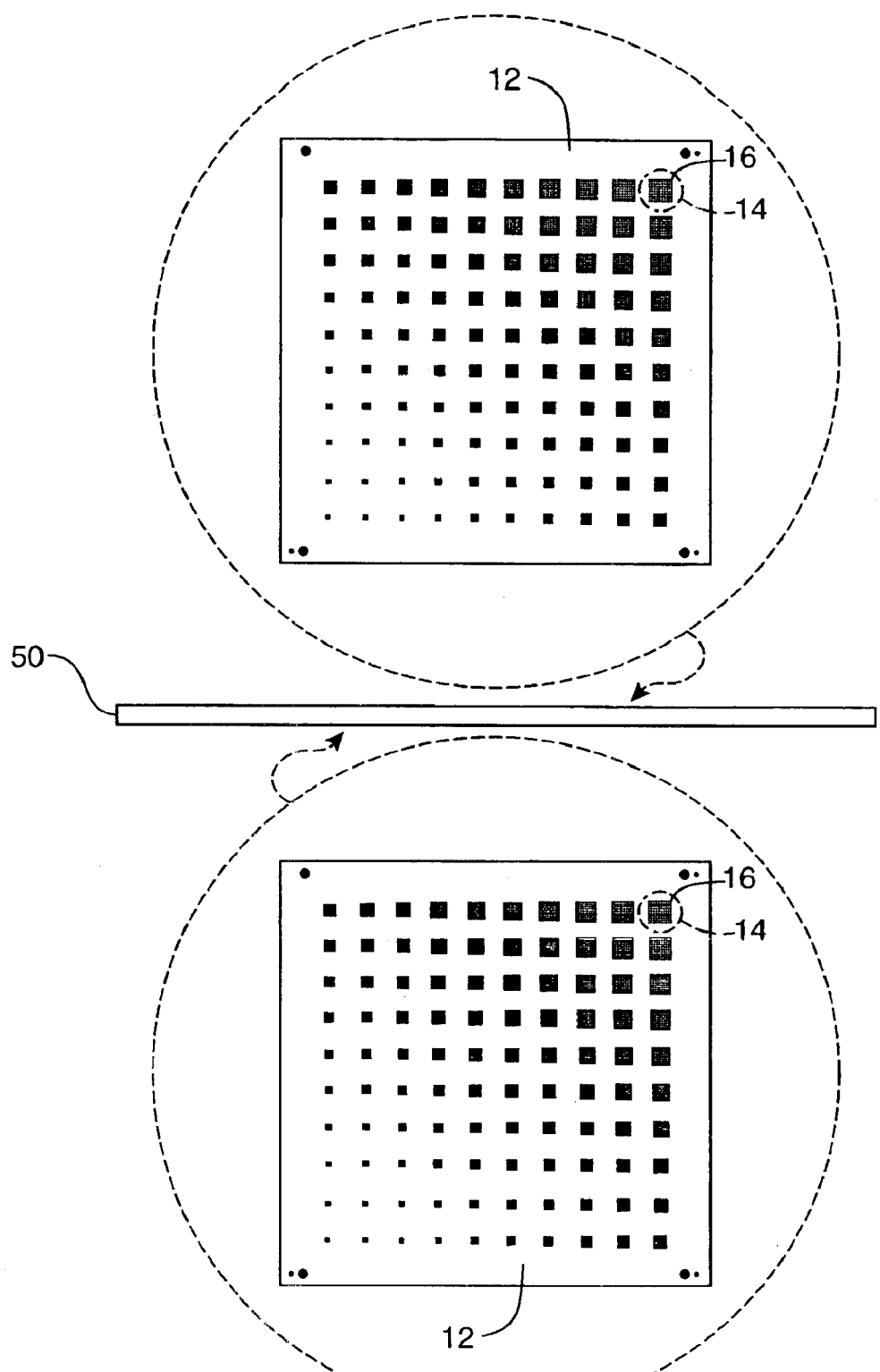
FIGS. 6a–6c are a series of diagrams showing views of top and bottom surfaces of a double-sided evaluation board in accordance with several different embodiments of the invention.
Figure 6B:
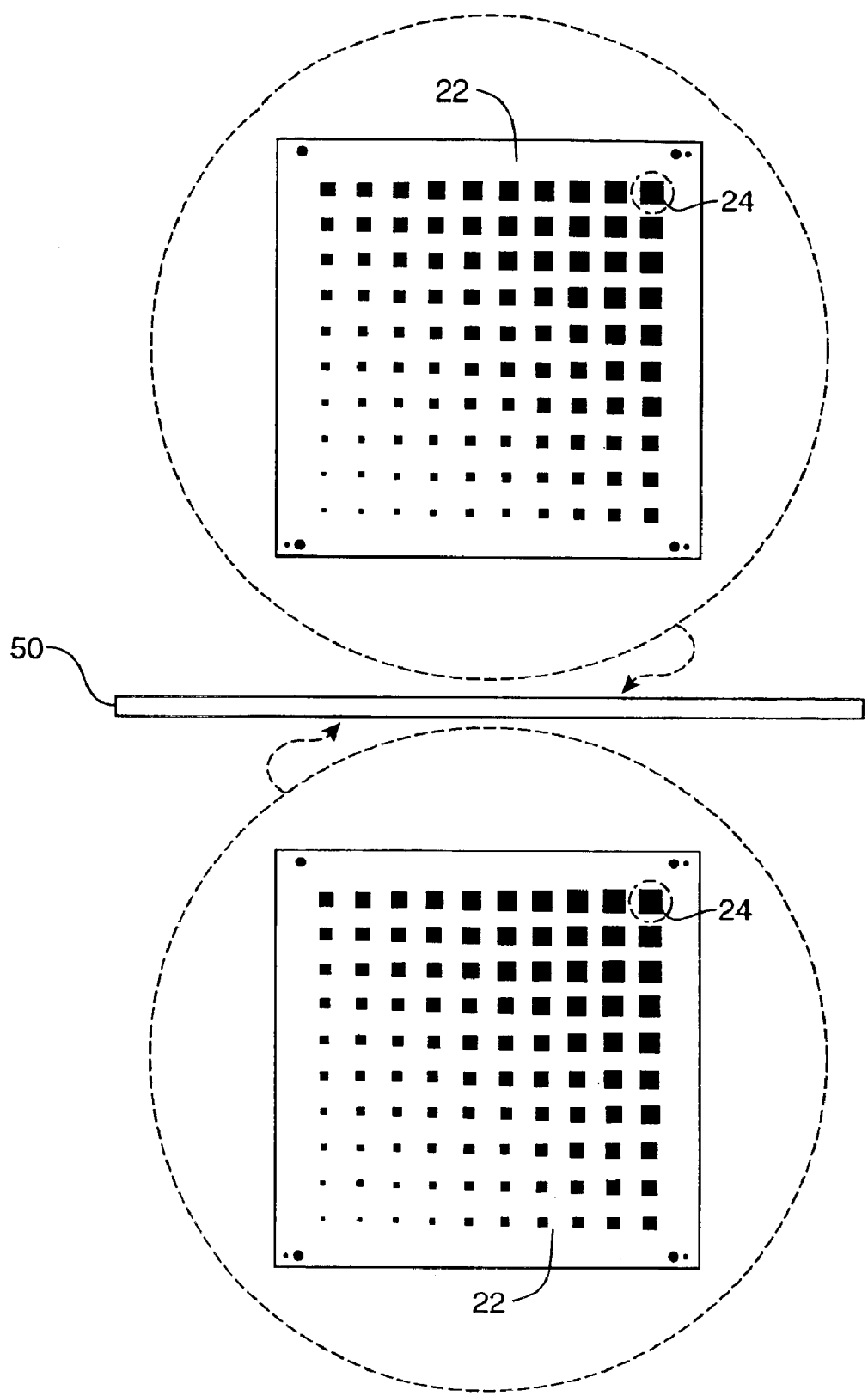
Figure 6C:
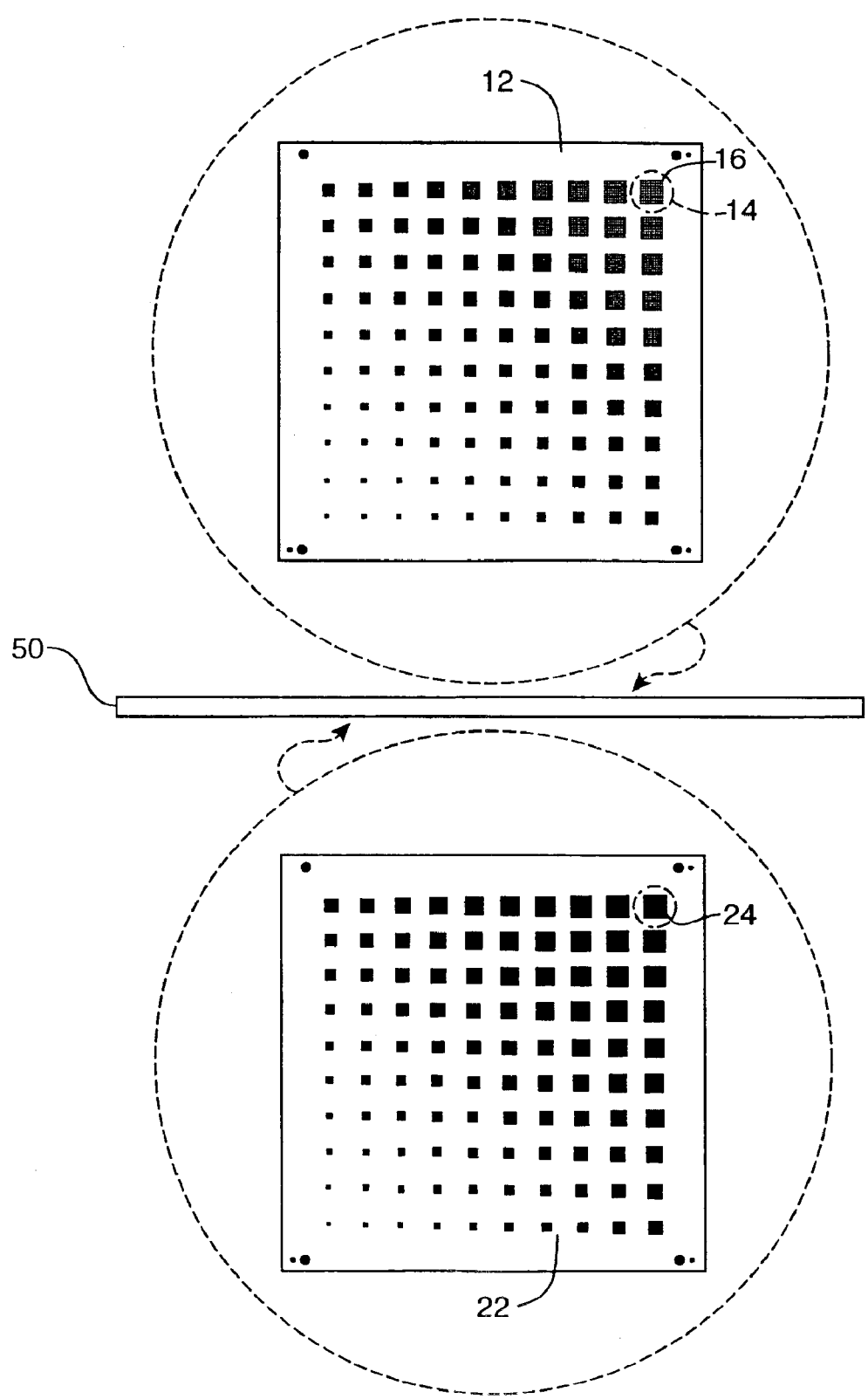

An evaluation board may have the board pad patterns of evaluation board 10 or evaluation board 20 on a single surface. Alternatively, an evaluation board 50 may be double sided and have the board pad patterns of evaluation board 10 on each surface (e.g. FIG. 6a), the board pad patterns of evaluation board 20 on each surface (e.g. FIG. 6b), or the board pad patterns of evaluation board 10 on one of the surfaces and the board pad patterns of evaluation board 20 on the other surface (e.g. FIG. 6c).

The evaluation boards 10 and 20 have been designed in an attempt to standardize paste/stencil/circuit board manufacturing. The evaluation board 10 can be used to effect SMT process trouble-shooting (one example being furnace profile optimization), for defect reduction and for manufacturability improvements. The evaluation board 10 can also be used to test the performance of different solder paste formulations that are provided by different manufacturers or the performance of different solder paste formulations provided by the same manufacturer for a given board pad size and pad-to-pad spacing as well as different printing and/or reflow parameters. The printability and wettability of the solder paste can also be investigated.

Evaluation board 10 may be used to conduct a variety of tests such as aperture tests, spread/slump tests and determination of solder sphere size applicability to a particular process/project. Aperture tests involve using the different pad-to-pad spacings of the evaluation board 10 to test the fine pitch capability of a particular solder paste formulation which could include a different powder and or flux formulation. Solder paste is the combination of solder spheres that are in a range of sizes for each particular solder sphere type (there are types 1–6 with type 3 being the most common). A higher type number corresponds to a smaller solder sphere size range which is also more expensive. The spread/slumping test can be used to test the slumping that occurs during the solder paste deposition (i.e. printing) stage of the SMT process and throughout the entire placement process until the solder paste is melted into solder. The different spacing of the solder paste on adjacent pads on the evaluation board 10, as a result of the different pad-to-pad spacing, can provide an indication of the severity of slumping. In addition, the proper solder sphere size in a solder paste needed to properly cover a particular a particular board pad size on the evaluation board 10 can be determined.

These various tests can be scored by observing the number of open pads and shorted pads (i.e. bridging) that occurs during various stages of the SMT process. The observation can be visually made through manual means (i.e. looking at the evaluation board with a high resolution microscope) or automated visual inspection means as is commonly known to those skilled in the art. The visual observations can be made since the solder paste usually consists of gray spheres in a usually clear organic gel and the board pads are typically either a reddish brown (copper) or a yellow (gold color). Accordingly, there is a good contrast between the solder paste and the board pads.

An open pad is a board pad that has no solder paste on it. Open pads provide an indication of the printability of the solder paste, the performance of the screen printer, stencil and/or the printing conditions. Open pads may also be examined after the reflow stage where the same conditions can be gauged as well as the ability of the solder paste to flow out and totally cover the pads and/or the effect of different reflow profile conditions.

A short can be the result of solder paste slumping in which the forces of gravity and the cohesive forces of the solder paste result in the solder paste spreading out and flattening so that two board pads are connected by the solder in the solder paste. This may occur because of the amount of solder paste, the amount/type of activated solder flux, the ratio of solder to flux, the board finish and/or the reflow profile conditions. Shorts can be checked for different board pad sizes, different pad-to-pad spacing and different reflow profiles. The evaluation board 10 can also be used to determine if there is a propensity of shorts in one region or another of the evaluation board 10. Shorts can also occur after the solder paste has melted.

Referring now to FIGS. 4a–4e, shown therein are several cases of deposited solder paste (i.e. a solder paste brick) on a board pad. FIG. 4a shows a preferable case in which a board pad 30 is adequately covered with a solder paste brick 32. FIG. 4b shows a case in which a board pad 34 is not adequately covered by a solder paste brick 36 (too little solder paste has been deposited). FIG. 4c shows a case in which a board pad 38 is also not adequately covered by a solder paste brick 40. In this case, enough solder paste has been deposited but it was incorrectly deposited partly outside of the board pad 38. FIG. 4d shows a case of an open pad 42 in which no solder paste has been deposited on the board pad 42. FIG. 4e shows a case of a short in which solder paste 44 and 45 from two adjacent board pads 46 and 48 have slumped together, shorting them together.

The evaluation board 20 may be used to provide test data on voids that occur for a particular solder paste formulation under certain SMT process parameters. In particular, the evaluation board 20 allows for the variation of stencil aperture and solder paste formulation to obtain an understanding of how large the board pad size and which pattern of board pad can be used without generating voids. Voids can form when a termination is placed on a solder pasted pad and put through the reflow process and there is either insufficient solder paste to cover the entire surface or the out gassing of the volatiles in the solder paste, board pad or component termination gets trapped when the solder paste is melted and then solidifies. In addition, the evaluation board 20 can be used to determine which solder paste formulation is better for reducing voids under certain SMT process parameters. X-ray techniques, as is commonly known to those skilled in the art, can be used to visually inspect for void formation. The evaluation board 20 can also be used for wetting tests to determine how much a particular solder paste formulation spreads or slumps after being applied to a PCB.

In addition, the evaluation boards 10 and 20 have features that mimic circuit boards that are used for manufacturing electronic devices. The evaluation boards 10 and 20 include solder masks in between the board pads. The evaluation boards 10 and 20 further comprise multiple alternating layers of fiberglass/epoxy and copper. This is advantageous for testing solder paste formulations that require different temperatures during the reflow stage. For instance, lead-free solder paste formulations require a higher temperature during the reflow process. The multi-layer construction of the evaluation boards 10 and 20 curtail the evaluation boards 10 and 20 from warping under the higher temperature. The multi-layer construction allows for the usage of actual reflow parameters that would usually be used during an actual SMT process which allows the solder paste to react as it would during an actual SMT process.

Another parameter that can be varied on the evaluation boards 10 and 20 for SMT process evaluation is the finish that is used on the evaluation board. For instance, a different finish, such as ENIG (Electroless Nickel Immersion Gold) or OSP (Organic Solderability Preservative) can be used to observe the effect of test board finish on a particular solder paste formulation that is being evaluated. An ENIG board is made by producing a board with copper pads by methods well known by those versed in the art. The boards are then put into the proper nickel containing bath for a predetermined length of time to deposit a specific range of nickel thickness by electrochemical means. After proper rinsing, the boards are then put into a gold containing electrochemical bath where the gold atoms spontaneously replace the surface nickel atoms until the entire nickel surface areas are covered by gold. An OSP board is made by producing a board with copper pads by methods well known by those versed in the art. The boards are then immersed in a water solution of chemicals that bond to the copper to form a layer of organocopper molecules that will protect the surface copper from oxidation over the length of time guaranteed by the board manufacturer.

Another advantage of the evaluation boards 10 and 20 is the square shape of the board which allows the board, and the stencil, to be rotated a multiple of 90 degrees (i.e. 90, 180, 270) and inserted into the SMT screen printer (the machine that applies the solder paste). This allows for evaluating different angles of the SMT printer so that for the machine it can be confirmed that there is no difference of process along both axes. For instance this feature allows for evaluating the effect of squeegee printing (top of stencil) and underside cleaning (bottom of the stencil) in different directions on the evaluation board 10(20).

In summary, the evaluation board 10 allows for a number of different tests to be conducted regarding SMT processing. In particular, the evaluation board 10 allows one to test:

1) the circuit board manufacturer's ability to create a circuit board with desired board pad sizes and pad-to-pad spacing;
2) the stencil manufacturer's ability to create a stencil with apertures having sizes and spacing that correspond with the board pad sizes and pad-to-pad spacing as well as different stencil manufacturing techniques (since for smaller apertures, a thinner stencil is required);
3) different printing and reflow environments with respect to the variables of time, temperature, humidity and the like;
4) different screen printer machines and screen printer parameters such as speed, pressure, etc. so that when a manufacturing company decides to buy equipment, the manufacturing company can evaluate different machines using the evaluation board to determine if the machine is going to meet current and future manufacturing needs;
5) printability of different solder pastes (i.e. different suppliers, different chemical formulations, different solder paste sphere size, etc.);
6) solder paste slump under both hot and cold conditions;
7) solder paste shorting;
8) insufficient solder paste; and,
9) solder shorts.

These test results can be evaluated in terms of the number of open and shorted pads for a given board pad size and pad-to-pad spacing.

In particular, when testing for slumping of solder paste or for pads that are shorted, the following guidelines can be followed:

1) Find rows and columns where the slumps or shorting occurs; 2) The smaller the pad-to-pad spacing and the board pad size where the slumping or shorting occurs, the better the paste, printer, printing conditions, etc.;
3) The rows and columns can be numbered to rate the solder paste. Slumping that causes a connection between two board pads is unwanted and the higher the number of connections between board pads (i.e. shorting), the worse the result.

In particular, when testing for open board pads the following guidelines can be followed:

1) Find rows and columns where the opens occur;
2) The smaller the pad-to-pad spacing and the board pad size where the slumping or shorting occurs, the better the paste, printer, printing conditions, etc.;
3) The rows and columns can be numbered to rate the solder paste. Open board pads are unwanted; the higher the number of open board pads, the worse the result.

Open board pads can be defined as complete or incomplete at the time of printing or reflow. For complete open board pads, in either the printing or reflow stage, solder paste is not at all present on a board pad. For incomplete open board pads at the printing stage, solder paste is present, but it is not covering all of the area of the board pad as expected. For incomplete open board pads at the reflow stage, reflowed solder paste has not flowed out to cover the expected area of the board pad.

It should be understood that various modifications can be made to the embodiments described and illustrated herein, without departing from the present invention, the scope of which is defined in the appended claims. For instance, the board pad patterns do not have to be arranged in a two-dimensional array. Other geometries could be used with repeatable patterns in which at least one of the board pad size and the pad-to-pad spacing is changed between each pattern.

In addition, there are many different shapes that can be used for the board pads as depicted in FIGS. 5a–5f. The board pad may be triangular (FIG. 5a), square (FIG. 5b), rectangular (FIG. 5c), dog-bone or dumbbell shaped (FIG. 5d), pentagonally shaped (FIG. 5e), C-shaped (FIG. 5f) or circular (FIG. 5g). In each of these cases, the shape may be rotated and the aspect ratio of the shape is variable. The dumbbell/dog-bone shape is particularly advantageous in determining open board pads under BGAs and CSPs. The dumbbell/dog-bone shape has a first circular member and a second, smaller circular member. The amount of solder paste that flows out from the larger, first circular member to the smaller, second circular member provides an indication of whether the board pad is open.

What is claimed is:

1. An evaluation board for evaluating one or more aspects of a surface mount technology system, the board comprising:
   a) a substrate having a surface;
   b) a plurality of board pad patterns formed on the surface, wherein each of the board pad patterns includes a plurality of board pads; and wherein at least some of the board pad patterns are arranged in a matrix wherein the size of board pads in adjacent board pad patterns progressively changes.

2. The evaluation board of claim 1, wherein at least some of the board pad patterns are arranged in a matrix wherein the pad-to-pad spacing of board pads in adjacent board pad patterns progressively changes.

3. The evaluation board of claim 1, wherein in each of said board pad patterns, the board pads have a uniform shape, size and pad-to-pad spacing.

4. An evaluation board for evaluating one or more aspects of a surface mount technology system, the board comprising:
   a) a substrate having a surface;
   b) a plurality of board pad patterns formed on the surface, wherein each of the board pad patterns includes a plurality of board pads; and wherein at least some of the board pad patterns are arranged in a matrix wherein the pad-to-pad spacing of board pads in adjacent board pad patterns progressively changes.

5. The evaluation board of claim 4, wherein in each of said board pad patterns, the board pads have a uniform shape, size and pad-to-pad spacing.

6. An evaluation board for evaluating one or more aspects of a surface mount technology system, the board comprising:
   a) a substrate having a surface;
   b) a plurality of board pad patterns formed on the surface, wherein each of the board pad patterns includes a plurality of board pads; and wherein at least some of the board pads patterns are arranged in a two dimensional matrix having rows and columns of board pad patterns, and wherein in each row of the matrix, a first characteristic of the board pads in the board pad pattern is varied and wherein in each column of the matrix, a second characteristic of the board pads in the board pad patterns is varied.

7. The evaluation board of claim 6, wherein the first characteristic is selected from the group consisting of: the shape; size; and pad-to-pad spacing of the board pads, and wherein the second characteristic is chosen from the group consisting of: the shape; size; and pad-to-pad spacing of the board pads, and wherein the first and second characteristics are different.

8. The evaluation board of claim 6, wherein in each of said board pad patterns, the board pads have a uniform shape, size and pad-to-pad spacing.

9. An evaluation board for evaluating one or more aspects of a surface mount technology system, the board comprising a substrate having two surfaces, wherein each surface has a plurality of board pad patterns formed on it, each board pad pattern comprising at least one board pad; wherein at least some of the board pad patterns are arranged in a matrix wherein at least one of the size and the pad-to-pad spacing of board pads in adjacent board pad patterns progressively changes.

10. The evaluation board of claim 9, wherein the first surface has a plurality of board pad patterns formed of board pads and wherein the second surface has a plurality of area-filled board pads.

11. The evaluation board of claim 9, wherein each of the two surfaces has a plurality of board pad patterns formed of board pads.

12. The evaluation board of claim 9, wherein each of the two surfaces has a plurality of area-filled board pads.

13. An evaluation board for evaluating one or more aspects of a surface mount technology system, the board comprising:
   a) a substrate having a surface;
   b) a plurality of board pad patterns formed on the surface, wherein each of the board pad patterns includes one of: an area-filled board pad or a plurality of board pads; wherein at least some of the board pad patterns are arranged in a matrix wherein at least one of the size and the pad-to-pad spacing of board pads in adjacent board pad patterns progressively changes.

14. The evaluation board of claim 13, wherein for each of the board pad patterns that includes a plurality of board pads, the board pads therein have a uniform shape, size and pad-to-pad spacing.

15. An evaluation board for evaluating one or more aspects of a surface mount technology system, the board comprising:
   a) a substrate having a surface;
   b) a plurality of board pad patterns formed on the surface, wherein each of the board pad patterns includes an area-filled board pad; and wherein at least some of the board pad patterns are arranged in a matrix wherein the size of area-filled board pads in adjacent board pad patterns progressively changes.

16. The evaluation board of claim 15, wherein at least some of the board pad patterns are arranged in a matrix wherein the pad-to-pad spacing of area-filled board pads in adjacent board pad patterns progressively changes.

17. An evaluation board for evaluating one or more aspects of a surface mount technology system, the board comprising:
   a) a substrate having a surface;
   b) a plurality of board pad patterns formed on the surface, wherein each of the board pad patterns includes an area-filled board pad; and wherein at least some of the board pad patterns are arranged in a matrix wherein the pad-to-pad spacing of area-filled board pads in adjacent board pad patterns progressively changes.

* * * * *

UNITED STATES PATENT AND TRADEMARK OFFICE
CERTIFICATE OF CORRECTION

PATENT NO.    : 6,888,360 B1
DATED         : May 3, 2005
INVENTOR(S)   : David James Connell and Beverly Howard Christian It is certified that error appears in the above-identified patent and that said Letters Patent is hereby corrected as shown below:

Title page,
Item [75], Inventor, replace "Beverly Howard Christian" with -- Beverley Howard Christian --

Column 6,
Line 25, replace "a particular a particular board" with -- a particular board --

Signed and Sealed this

Twelfth Day of July, 2005

JON W. DUDAS
*Director of the United States Patent and Trademark Office*